US00PP15631P2

(12) United States Plant Patent
Sanders

(10) Patent No.: US PP15,631 P2
(45) Date of Patent: Mar. 8, 2005

(54) ***AGERATUM* PLANT NAMED 'AGROSAMTIS'**

(50) Latin Name: *Ageratum houstonianum*
Varietal Denomination: Agrosamtis

(75) Inventor: Monica Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 85 days.

(21) Appl. No.: 10/817,496

(22) Filed: Apr. 1, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Edouard G. Lebel

(57) ABSTRACT

A new *Ageratum* plant, characterized particularly as to novelty by light purple red flowers, early and continuously flowering and has a growing habit that is flat, well branched and vigorous.

1 Drawing Sheet

Latin name of the genus and species of the plant claimed: *Ageratum houstonianum.*
Varietal denomination: 'Agrosamtis'.

BACKGROUND OF THE NEW PLANT

The present invention comprises a new distinct cultivar of *Ageratum,* botanically known as *Ageratum houstonianum.*

The new variety "Agrosamtis" was discovered as a seedling variant of a population of rose and pink flowering plants in a controlled planting.

As a result of this the present cultivar was created in 2000 in Enkhuizen, Netherlands and has been repeatedly asexually reproduced by cuttings in Enkhuizen, Netherlands, in Gilroy, USA, in Angers, France and in Sarrians, France over a three year period. The distinctive characteristics of this new *Ageratum* are stable and reproduced true to type in successive generations of asexual reproduction. It takes 8 to 10 weeks to produce a finished plant, depending on the temperature.

This new *Ageratum* plant is an annual in most climatical zones in the US, only in zones 9 and 10 it is a perennial plant.

DESCRIPTION OF THE DRAWING

This new *Ageratum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Ageratum.* The data which defines these characteristics were collected from asexual reproductions carried out in Enkhuizen, Netherlands. The plant history was taken on 30 weeks old plants, blossomed under natural light in a greenhouse.

Color readings were taken in the greenhouse under ambient light. Color references are primarily to The R.H.S. Colour Chart of The Royal Horticultural Society of London.

Differences between the new cultivar 'Agrosamtis,' and a similar cultivars

| | 'Agrosamtis' | 'Agsantis' | 'Agmontis' |
|---|---|---|---|
| Flower color | Light red purple | Light purple | Purple |
| Plant height | 15–20 cm | 15–20 cm | 20–25 cm |
| Diameter of plant | 30–35 cm | 35–40 cm | 35–40 cm |

The plant:
- *Classification—Botanical.—Ageratum houstonianum.*
- *Parentage.*—Population of rose and pink flowering plants.
- *Growth habit.*—Ascending, well branched.
- *Plant height.*—15–20 cm.
- *Spreading area of plant.*—30–35 cm.
- *Growth rate.*—Compact.
- *Strength.*—Very good.
- *Branching character.*—Freely branching and lateral branching at every node.
- *Blooming period.*—Year round.

The stem:
- *Stem length.*—3–9 cm.
- *Diameter.*—1–2 mm.
- *Shape.*—Round.
- *Color.*—145 C.
- *Anthocyan pigmentation.*—Absent.
- *Length of internode.*—5–17 mm, depending on the light where the plant is propagated.
- *Pubescence.*—Slightly pubescent.

The foliage:
- *Phyllotaxis.*—Opposite, decussate.
- *Shape of blade.*—Cordate.
- *Texture.*—Upper side: Slightly pubescent. Lower side: Slightly pubescent.
- *Venation.*—Reticulate.
- *Leaf margin.*—Serrate.
- *Leaf base.*—Cordate.
- *Leaf apex.*—Rounded.
- *Length.*—7–21 mm.
- *Width.*—5–17 mm.
- *Colour.*—Upper side: Dark green 137 B. Lower side: Medium green 138 B.

*Pubescence*.—Some pubescence is present.
*Length of petiole*.—1–5 mm.
*Diameter of petiole*.—1–2 mm.
*Color of petiole*.—Light green 145 C.
*Petiole surface texture*.—Slightly pubescent.

Inflorescence:
*Inflorescence*.—Compound umbel of capitula.
*Number of inflorescence per plant*.—40–50.
*Umbel size*.—3,0–5,0 cm.
*Umbel depth*.—1,5–3,0 cm.
*Length of peduncle*.—4–23 mm.
*Diameter of peduncle*.—1–2 mm.
*Color of peduncle*.—RHS 144 B.
*Length of pedicel*.—2–9 mm.
*Diameter of pedicel*.—1 mm.
*Color of pedicel*.—RHS 144 B.
*Number of capitula per inflorescence*.—2–4.
*Number of disc florets per capitulum*.—40–75.
*Capitulum in bud stage*.—Round, flat capitulum, showing unopened florets from the start.
*Number of ray florets*.—0.
*Shape of the corolla of the disk floret*.—Actimorphic.
*Number of lobes*.—5.
*Length of disk floret*.—3–4 mm.
*Diameter of disk floret*.—1–2 mm.
*Color of disk floret upper side*.—RHS N66 D.
*Color of disk floret lower side*.—RHS 155C.
*Number of phyllaries per capitulum*.—15–20.
*Length of phyllaries*.—3 mm.
*Diameter of phyllaries*.—1 mm.
*Color of phyllaries upperside*.—RHS 143 C. Innerside RHS 143 C.
*Diameter of capitulum at beginning of flowering*.—3–4 mm.
*Depth of capitulum*.—5–7 mm.
*Color of capitulum at beginning of flowering*.—RHS 064 D.
*Diameter of capitulum at full flowering*.—8–10 mm.
*Color of capitulum at full flowering*.—RHS 065 A.
*Color of capitulum when old*.—RHS 069 D.

Reproductive organs:
*Gynoecium*.—Number of pistils: 1.
*Shape of pistils*.—Style with two filiform branches.
*Length of stigma and style*.—2–3 mm.
*Color of stigma*.—RHS 065 A.
*Inferior ovary*.—5 ribbed.
*Pappus*.—Short.
*Androecium*.—
*Number of anthers*.—5, connate in a tube, filaments free.
*Shape of anthers*.—Calcarate.
*Pollen*.—A little pollen is present.
*Color of pollen*.—RHS N155 A.
*Fragrance*.—No fragrance.
*Lastingness of the bloom*.—The capitula of one umbel open over a period of 3 to 4 weeks.
*Seedset*.—'Agrosamtis' has seedset.

Seed:
*Shape*.—Pentagonal.
*Length*.—2 mm.
*Diameter*.—0.8 mm.
*Color*.—RHS 202 A.
*Pappus*.—Very short.

Roots:
*Type of roots*.—Fibrous. Roots start to grow on every part of the stem that contacts de soil, so not only at the nodes.

Physiological and ecological characteristics. Good tolerance to heat and cold, but no frost tolerance. Strong resistance to pests and diseases.

What is claimed is:

1. A new and distinct cultivar of *Ageratum* plant named 'Agrosamtis,' as substantially illustrated and described herein.

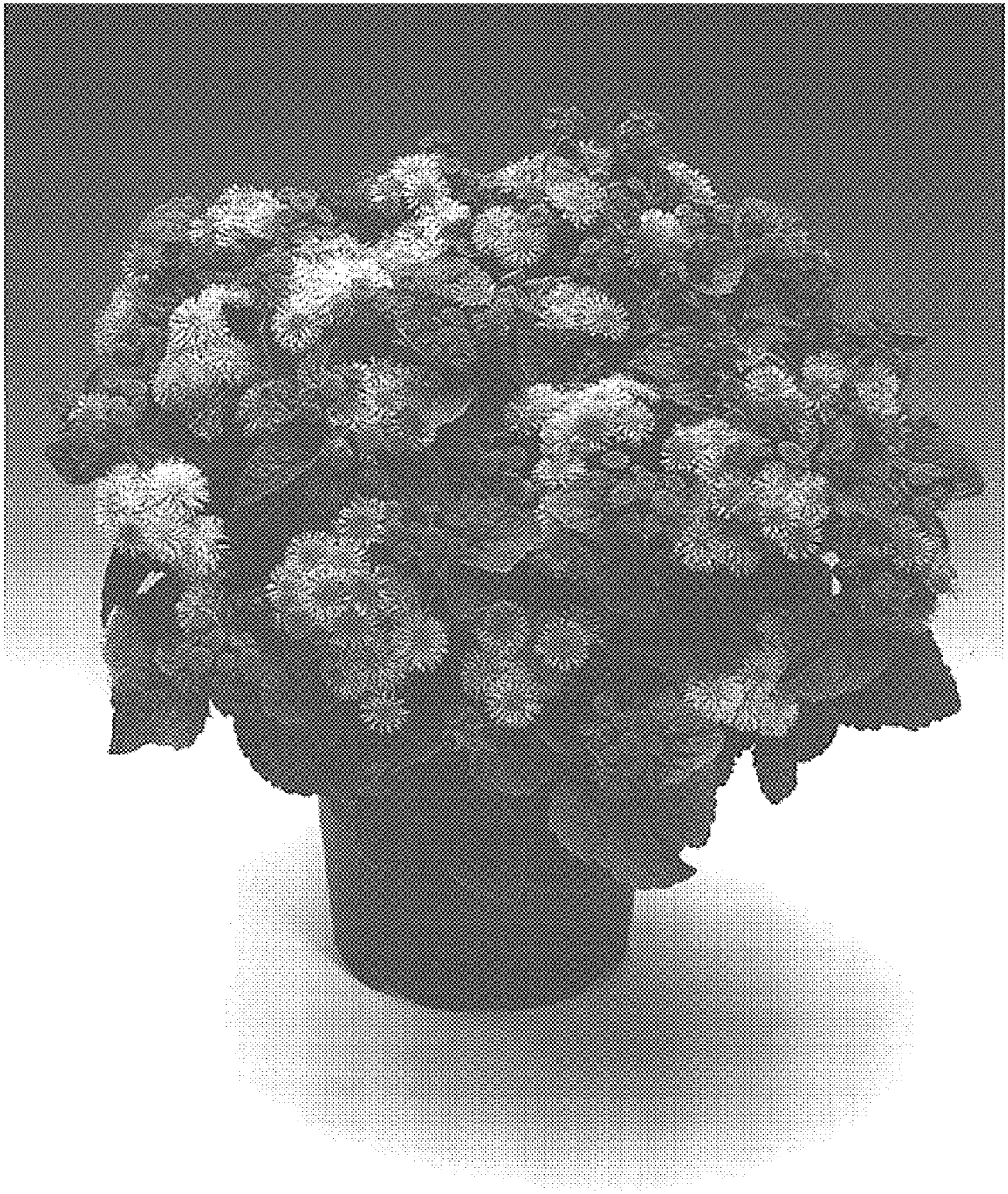

* * * * *